United States Patent
Gaber

(10) Patent No.: US 6,491,645 B1
(45) Date of Patent: *Dec. 10, 2002

(54) UTERINE TISSUE COLLECTOR

(76) Inventor: Benny Gaber, Oren Street 29, 34735 Haifa (IL)

(*) Notice: Subject to any disclaimer, the term of this patent is extended or adjusted under 35 U.S.C. 154(b) by 0 days.

This patent is subject to a terminal disclaimer.

(21) Appl. No.: 09/674,590

(22) PCT Filed: Mar. 23, 1999

(86) PCT No.: PCT/IL99/00164

§ 371 (c)(1),
(2), (4) Date: Dec. 21, 2000

(87) PCT Pub. No.: WO99/56628

PCT Pub. Date: Nov. 11, 1999

(30) Foreign Application Priority Data

May 7, 1998 (IL) .................................................. 124361

(51) Int. Cl.[7] .............................................. A61B 10/00
(52) U.S. Cl. ........................................ 600/571; 604/19
(58) Field of Search ................................ 600/562, 565, 600/569, 570, 571, 572, 573, 582, 581, 585, 433–435; 606/160; 604/19, 35, 36, 38, 164.09, 164.13

(56) References Cited

U.S. PATENT DOCUMENTS

| 3,721,244 A | * | 3/1973 | Elmaleh | 604/128 |
|---|---|---|---|---|
| 4,010,737 A | | 3/1977 | Vilaghy et al. | 600/567 |
| 4,340,066 A | | 7/1982 | Shah | 600/562 |
| 4,627,444 A | * | 12/1986 | Brooker | 600/571 |
| 4,893,635 A | | 1/1990 | de Groot et al. | 600/567 |
| 4,895,166 A | | 1/1990 | Farr et al. | 600/564 |
| 4,998,916 A | | 3/1991 | Hammerslag et al. | 604/95 |
| 5,069,224 A | | 12/1991 | Zinnanti, Jr. | 600/565 |
| 5,176,646 A | | 1/1993 | Kuroda | 604/154 |
| 5,217,479 A | | 6/1993 | Shuler | 606/180 |
| 5,224,488 A | | 7/1993 | Neuffer | 600/564 |
| 5,285,795 A | * | 2/1994 | Ryan et al. | 600/563 |
| 5,335,671 A | | 8/1994 | Clement | 600/566 |
| 5,345,937 A | * | 9/1994 | Middleman et al. | 600/434 |
| 5,431,673 A | | 7/1995 | Summers et al. | 606/170 |
| 5,454,827 A | | 10/1995 | Aust et al. | 606/170 |
| 5,715,832 A | | 2/1998 | Koblish et al. | 600/564 |
| 5,797,883 A | * | 8/1998 | Prince | 604/170.01 |
| 5,810,861 A | | 9/1998 | Gaber | 600/571 |
| 5,951,490 A | * | 9/1999 | Fowler | 600/571 |
| 6,042,552 A | * | 3/2000 | Cornier | 600/562 |

FOREIGN PATENT DOCUMENTS

| EP | 0 521 595 A2 | | 1/1993 |
|---|---|---|---|
| FR | 2 602 414 | | 2/1988 |
| WO | WO 91/13355 | | 9/1991 |
| WO | WO 93/07597 | | 4/1993 |
| WO | WO 94/04078 | | 3/1994 |
| WO | WO 95/01128 | | 1/1995 |
| WO | WO 96/26676 | | 9/1996 |
| WO | WO-99/12476 A | * | 3/1999 |

OTHER PUBLICATIONS

Pipelle de Cornier, Prodimed (France) Endometrial Suction Curette, pp. 1–5, 1984.

* cited by examiner

*Primary Examiner*—Kevin Shaver
*Assistant Examiner*—Charles Marmor, II
(74) *Attorney, Agent, or Firm*—Marshall, Gerstein & Borun

(57) ABSTRACT

A uterine tissue collector including a cannula which has an aperture formed therein through which tissue material can be sucked into a lumen formed in the cannula, at least one guide wire attached to a distal portion of the cannula, wherein movement of the at least one guide wire flexes the distal portion of the cannula, and a suction device operative to suck tissue material into the lumen, characterized by the suction device comprising a syringe comprising a distal barrel which extends from a proximal barrel, the proximal barrel having a larger diameter than the distal barrel.

9 Claims, 2 Drawing Sheets

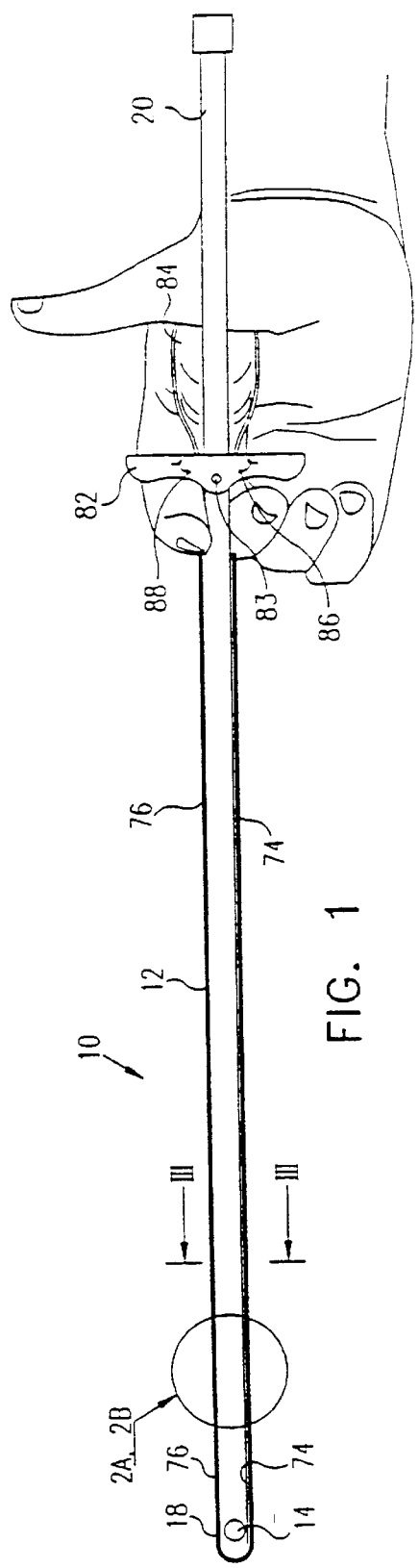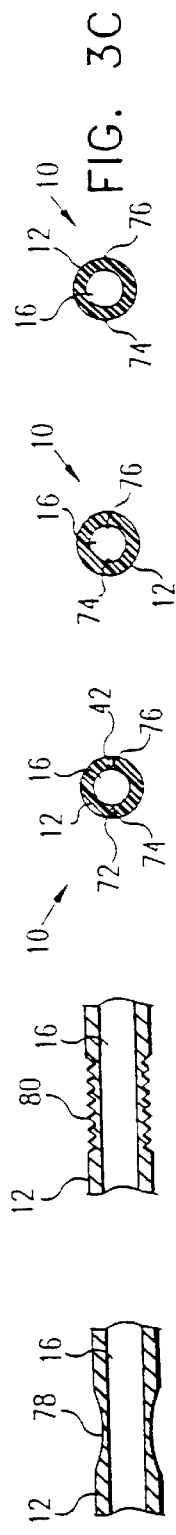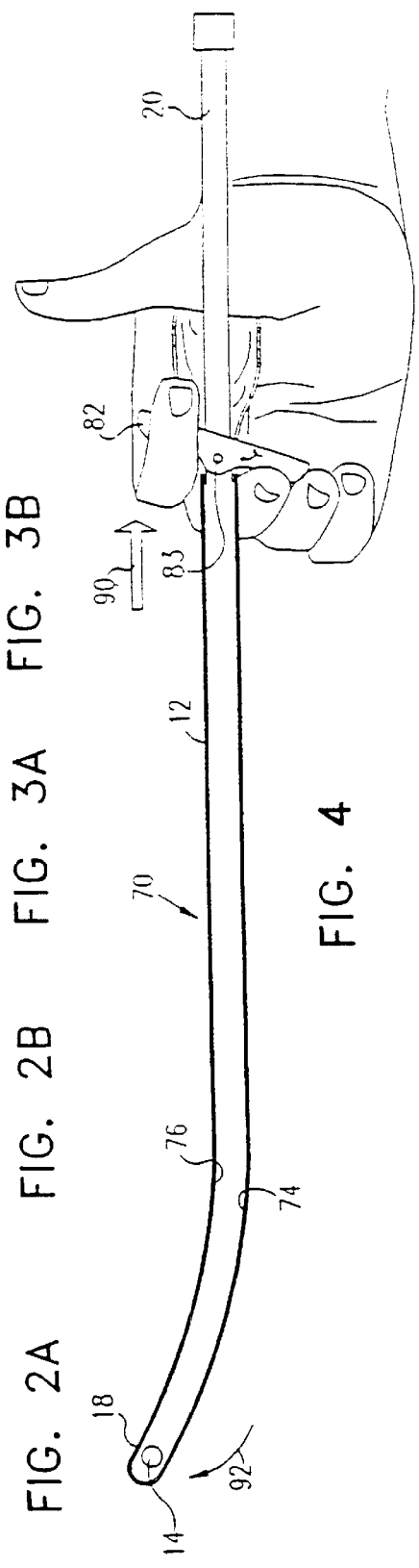

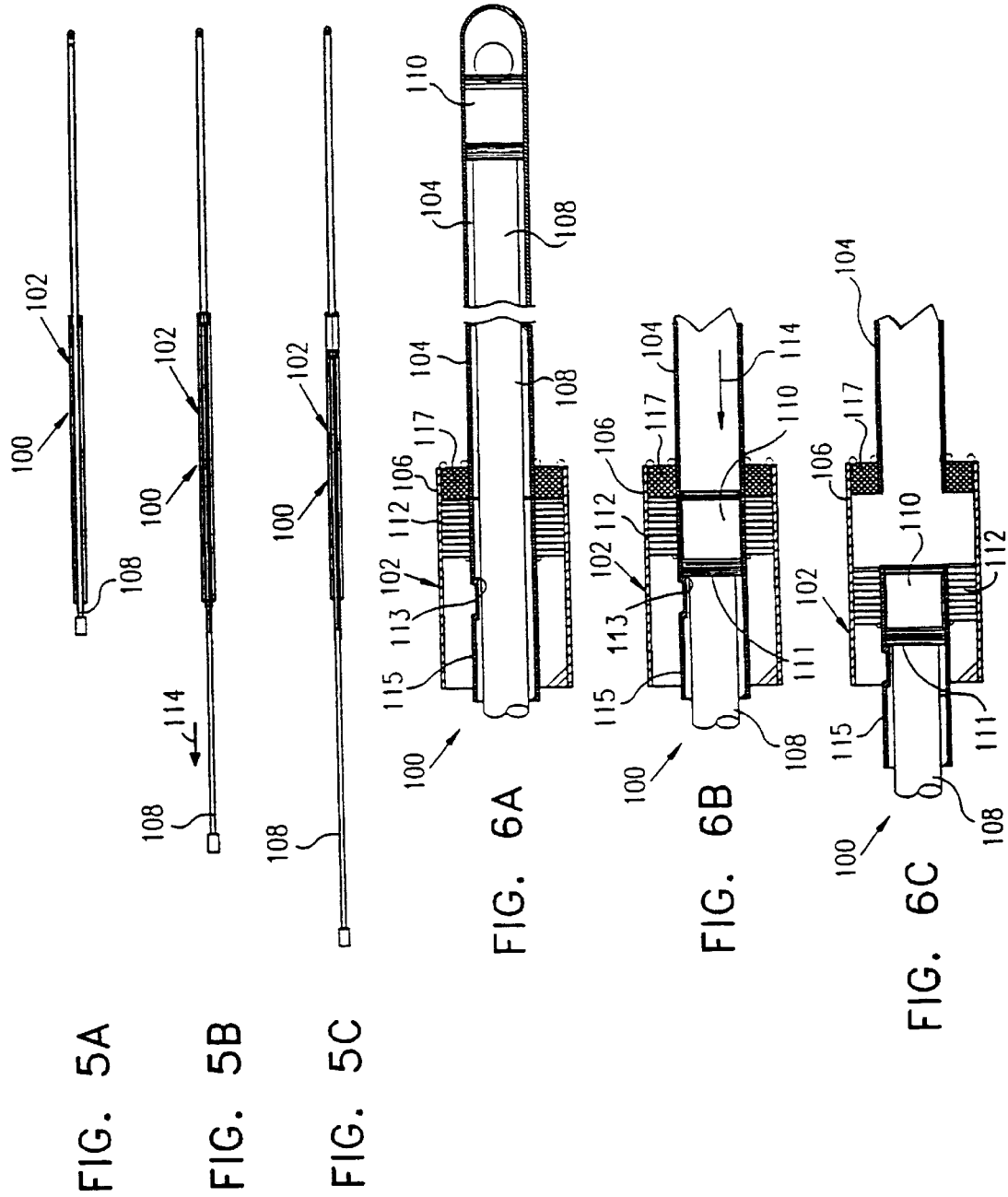

UTERINE TISSUE COLLECTOR

FIELD OF THE INVENTION

The present invention relates to gynecological instruments generally, and particularly to a uterine tissue collector which scrapes a uterus and collects scraped uterine material by suction.

BACKGROUND OF THE INVENTION

Obtaining samples of cervical and uterine tissue is normally performed in the art by one of three methods: dilation of the cervix and curettage of the endometrium, known as D & C; suction without dilation of the cervix via a small diameter tube, known as aspiration; or by suction curettage. D & C and suction curettage are capable of collecting as much cervical or uterine material as required, but require anesthesia. Aspiration with a small diameter tube does not normally require anesthesia but is not capable of obtaining amounts of tissue comparable to those obtainable with D & C. In order to obtain amounts of tissue comparable to those obtainable with D & C, aspiration must be performed with a large tube which requires anesthesia.

An endometrial suction curette, called the Pipelle de Cornier, manufactured by PRODIMED of France, may be used to scrape endometrial material with the distal end of a sheath of the curette. However, the scraping area is limited by the relatively small diameter of the sheath and the "spaghetti-like limpness" of the curette.

There are several instruments in the patent literature for scraping a uterus and/or collecting scraped material. U.S. Pat. No. 5,224,488 to Neuffer describes a biopsy needle insertable into a body with a deformable strip which can cut tissue and which protrudes laterally outwards of the needle. The strip does not move back and forth but rather cuts when the user rotates the needle about its axis. The strip is manually pushed laterally outwards of the needle by turning a screw.

U.S. Pat. No. 4,895,166 to Farr describes a rotatable cutter for penetrating into and cutting tissue in a lumen (body cavity). The cutting tool includes two spaced external segments of a conical generally hollow portion with cutting surfaces at their edges. A vacuum is applied to remove fragments of cut tissue. Again the cutter cuts by rotating, not by moving back and forth.

U.S. Pat. No. 5,217,479 to Shuler describes a rotary surgical cutting instrument which cuts with an inner member rotating inside an outer member. The inner member is provided with two symmetric rows of triangular cutting teeth and the outer member has a distal cutting aperture. Here, too, the instrument cuts by rotating, not by moving back and forth.

U.S. Pat. No. 4,340,066 to Shah describes an endometrial sampling device including a cannula which has a transverse slot with scraping edges and a sharp point, and which is insertable into the cervix. By manually moving the cannula and scraping with the scraping edges, one can collect endometrial tissue. The cutter cuts by manually moving the cannula and scraping material, and not by moving back and forth.

U.S. Pat. No. 5,335,671 to Clement describes a surgical assembly for removal of body tissue including a movable cutter inside a cannula which is insertable into a desired location in a patient. The cutter is rigid and cuts by shearing against an aperture in the cannula. A vacuum may be provided for removing cut material. The cutter cuts by shearing in one direction, not by moving back and forth.

Applicant/assignee discloses in PCT Patent Application PCT/US96/02702 and U.S. patent application Ser. No. 08/607,901, the disclosure of which is incorporated herein by reference, a uterine tissue collector including a deformable scraper which is capable of being deformed from an undeformed configuration to a deformed configuration. The scraper scrapes a uterus while moving between the undeformed configuration and the deformed configuration. This uterine tissue collector has already enjoyed much success in clinical trials.

SUMMARY OF THE INVENTION

The present invention seeks to provide an improved uterine tissue collector which preferably includes a pair of guide wires that can be used to bend or flex a cannula of the tissue collector to and fro. The cannula is flexible or is constructed with notches or a thin-walled section, so that the cannula tip is bendable. The distal ends of the guide wires are attached to a distal portion of the cannula, and the proximal ends of the guide wires are attached to a finger or hand controlled lever. By pulling on the lever to the right or left, the distal portion of the cannula is accordingly bent or flexed, thereby significantly increasing the area which may be scraped and/or raked. The guide wires may be passed through lumens formed in the cannula or may be internal or external to the cannula.

The present invention also provides a suction device constructed as a two-stage syringe. The syringe has a double barrel, a distal barrel which extends from a proximal barrel, the proximal barrel having a larger diameter than the distal barrel. A plunger sealingly slides in the distal barrel like any conventional plunger. When the plunger is completely pulled proximally through the distal barrel and enters the proximal barrel, the distal tip of the plunger is pulled into engagement with a plunger element so that the plunger element is fixed to the distal tip of the plunger. The plunger element now acts as a new tip of the plunger in its travel in the proximal barrel. Since the proximal barrel has a larger area than the distal barrel, the amount of material which can be collected with the syringe is significantly greater than a conventional syringe of the prior art which has only one barrel of the size of the distal barrel of the present invention, and yet the smaller diameter of the distal barrel allows entry of the syringe of the present invention into smaller openings than possible with syringes of the prior art which have a single barrel of the size of the proximal barrel. Additionally, the arrangement of the proximal and distal barrels ensures a very efficient discharge of all the material collected by the uterine scraper when the plunger is pushed distally to expel the collected material for examination purposes.

As mentioned before, the scraping swath of prior art curettes is significantly limited by the limpness of the curette. In contrast, the combination of the larger diameter proximal barrel and smaller diameter distal barrel provides a structure which is significantly stiffer than the single-diameter curettes of the art. For example, if the distal barrel is one-half the length of a prior art curette, the distal barrel is 8 times stiffer in bending. Of course, the distal barrel is not so rigid that it cannot be bent at all. Rather the combination of the guide wires which flex the distal barrel plus the greater stiffness of the distal barrel, provides a significantly larger scraping swath than was ever possible heretofore in the art.

It is noted that throughout the specification and claims, the term "uterine tissue" refers to any material in the cervical canal and uterine cavity, e.g. uterine layering, cervical mucosa, gestational products, endometrium or tumoral substances. In the specification and claims, the term "uterus" encompasses the cervical canal and uterine cavity.

There is thus provided in accordance with a preferred embodiment of the present invention a uterine tissue collector including a cannula which has an aperture formed therein through which tissue material can be sucked into a lumen formed in the cannula, and at least one guide wire attached to a distal portion of the cannula, wherein movement of the at least one guide wire flexes the distal portion of the cannula.

In accordance with a preferred embodiment of the present invention the at least one guide wire is disposed through a lumen formed through the cannula.

Further in accordance with a preferred embodiment of the present invention the lumen constrains movement of the at least one guide wire in a direction generally along a longitudinal axis of the cannula.

Still further in accordance with a preferred embodiment of the present invention a proximal portion of the at least one guide wire is pivotally attached about a fulcrum to a lever such that movement of the lever flexes the distal portion of the cannula.

Additionally in accordance with a preferred embodiment of the present invention a pair of such guide wires are provided, wherein generally proximal movement of one of the guide wires causes flexing of the distal portion of the cannula in a direction generally opposite to that caused by generally proximal movement of the other guide wire. Preferably each guide wire is disposed in a separate lumen formed in the cannula.

In accordance with a preferred embodiment of the present invention the at least one guide wire is sufficiently stiff so as to be able to push as well as pull the distal portion of the cannula.

There is also provided in accordance with a preferred embodiment of the present invention a uterine tissue collector including a cannula adapted for insertion into a uterus, the cannula including a scraper for scraping the uterus, and a suction device which sucks material scraped by the scraper, characterized by the suction device including a syringe including a distal barrel which extends from a proximal barrel, the proximal barrel having a larger diameter than the distal barrel, a plunger element disposed about a tube inside the proximal barrel, the plunger element being adapted to sealingly slide inside the proximal barrel, and a plunger that passes through the tube and the plunger element, wherein when the plunger is pulled proximally and starts to enter the proximal barrel, a proximal face of a distal end of the plunger abuts against a shoulder formed in the tube, such that when the plunger is pulled further proximally, the plunger moves together with the tube and the plunger element serves as a new distal end of the plunger during sliding travel in the proximal barrel. Preferably the tube guides and supports the plunger during its travel in the distal barrel. Preferably the uterine tissue collector of the present invention combines both the steering feature and the double barrel suction device feature.

BRIEF DESCRIPTION OF THE DRAWINGS

The present invention will be understood and appreciated more fully from the following detailed description, taken in conjunction with the drawings in which:

FIG. 1 is a simplified pictorial illustration of a uterine tissue collector constructed and operative in accordance with a preferred embodiment of the present invention, the uterine tissue collector including a guide wire which flexes a bendable cannula;

FIGS. 2A and 2B are simplified enlarged illustrations of two different configurations of a bendable portion of the cannula of FIG. 1;

FIGS. 3A, 3B and 3C are simplified, enlarged sectional illustrations of the cannula of FIG. 1, showing three different configurations for passage of guide wires;

FIG. 4 is a simplified pictorial illustration of the uterine tissue collector of FIG. 1 being flexed by a user;

FIGS. 5A, 5B and 5C are simplified pictorial illustrations of a suction device, useful with a uterine tissue collector such as any of the uterine tissue collectors of the present invention, constructed and operative in accordance with a preferred embodiment of the present invention, with a plunger fully pushed into a distal barrel of a syringe, with the plunger proximally retracted from the distal barrel and prior to entry into a proximal barrel of the syringe, and with the plunger retracted into the proximal barrel, respectively; and FIGS. 6A, 6B and 6C are enlarged simplified pictorial illustrations of the suction device corresponding to FIGS. 5A, 5B and 5C.

DETAILED DESCRIPTION OF A PREFERRED EMBODIMENT

Reference is now made to FIG. 1 which illustrates a uterine tissue collector 10 constructed and operative in accordance with a preferred embodiment of the present invention.

Uterine tissue collector 10 includes a hollow cannula 12 shaped for insertion into a uterus. Cannula 12 may be straight or bent. Cannula 12 has an aperture 14, formed at a distal portion 18 of cannula 12, which has a rim that can be used to scrape tissue material. A plunger 20 which is disposed in cannula 12 can be used to suck the scraped material into a central lumen 16. In a preferred embodiment of the present invention, plunger 20 and cannula 12 form a disposable assembly. After discharging the collected uterine material into a vial containing a preserving solution such as formalin, the material is then ready for pathological examination, and the assembly may be discarded.

Referring additionally to FIG. 3A, uterine tissue collector 10 includes a second lumen 42 and a third lumen 72 which serve as passageways for a pair of guide wires 74 and 76 which can be used to flex cannula 12. Alternatively, as seen in FIG. 3B, guide wires 74 and 76 may be disposed inside lumen 16. Still alternatively, as seen in FIG. 3C, guide wires 74 and 76 may be disposed outside cannula 12. As seen in FIG. 1, the distal ends of guide wires 74 and 76 are attached near distal portion 18 of cannula 12. The cannula is preferably constructed of a flexible material. Additionally or alternatively, a portion of cannula 12 may be constructed with a relatively low bending moment to permit easy flexing of distal portion 18 of cannula 12. For example, as seen in FIG. 2A, cannula 12 may have a thin-walled section 78, or as seen in FIG. 2B, cannula 12 may be formed with one or more notches 80 so as to make the cannula tip bendable sideways. Thin-walled section 78 and notches 80 may be formed around a portion of the perimeter of cannula 12 or all around the perimeter.

As seen in FIG. 1, the proximal ends of guide wires 74 and 76 are attached to a finger or hand controlled lever 82. Lever 82 is preferably pivotally attached about a fulcrum 83 to a handpiece 84 which fits comfortably in the hand of a user.

Guide wires 74 and 76 are preferably bent about attachment points 86 and 88, respectively, in lever 82. As seen in FIG. 4, by pulling on lever 82, such as with the index finger, in the direction of an arrow 90, distal portion 18 of cannula 12 is accordingly bent or flexed generally in the direction of an arrow 92. The flexing action significantly increases the area which may be scraped and/or raked with uterine tissue collector 10.

The skilled artisan will appreciate that a single guide wire may be employed which has sufficient stiffness to push as well as pull the distal portion 18 of cannula 12. In addition, instead of hand lever 82, it is appreciated that guide wires 74 and 76 may be attached to a motor for automatic flexing, if desired.

Reference is now made to FIGS. 5A–6C which illustrate a suction device 100, useful with uterine tissue collector 10. For the sake of clarity, uterine tissue collector 10 is not illustrated in FIGS. 5A–6C with guide wires 74 and 76 and lever 82. Suction device 100 comprises a two-stage syringe 102. Syringe 102 preferably includes a distal barrel 104 which extends from and is in fluid communication with a proximal barrel 106, proximal barrel 106 having a larger diameter than distal barrel 104. A plunger 108, having a distal end 110, sealingly slides in distal barrel 104 like any conventional plunger, such as plunger 20 shown in FIGS. 1 and 4. The body of plunger 108 passes through a plunger element 112 which comprises a tube 115 next to a distal face 117 of proximal barrel 106. Tube 115 guides and supports plunger 108 during its travel in distal barrel 104. Plunger element 112 is sized to sealingly slide in proximal barrel 106.

As seen in FIG. 6B, when plunger 108 is pulled proximally in the direction of an arrow 114 and starts to enter proximal barrel 106, a proximal face 111 of the distal end 110 of plunger 108 abuts against a shoulder 113 formed in tube 115. Upon further proximal pulling in the direction of arrow 114, plunger 108 now moves together with tube 115 and plunger element 112, while distal barrel 104 remains stationary. Plunger element 112 is fixed together with tube 115. Thus, plunger element 112 now acts as a new distal end of plunger 108 in its travel in proximal barrel 106.

Since proximal barrel 106 has a larger area than distal barrel 104, the amount of material which can be collected with syringe 102 is significantly greater than a conventional syringe of the prior art which has only one barrel of the size of the distal barrel of the present invention, and yet the smaller diameter of distal barrel 104 allows entry of syringe 102 into smaller openings than possible with syringes of the prior art which have a single barrel of the size of proximal barrel 106.

Material collected with syringe 102 may be discharged by distally pushing tube 115 together with plunger 108 in the direction opposite to arrow 114. Once plunger element 112 is pushed back to abut against distal face 117 of proximal barrel 106 (the position shown in FIG. 6B), distal end 110 of plunger 108 becomes dislodged from plunger element 112 and is free to be pushed further into distal barrel 104, again in the direction opposite to arrow 114. Plunger 108 may then be further pushed to completely discharge all the collected material.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A uterine tissue collector comprising:
   a cannula which has an aperture formed therein through which tissue material can be sucked into a lumen formed in said cannula;
   at least one guide wire attached to a distal portion of the cannula, wherein movement of said at least one guide wire flexes the distal portion of said cannula; and
   a suction device operative to suck tissue material into said lumen;
   characterized by said suction device comprising:
      a syringe comprising a distal barrel which extends from a proximal barrel, said proximal barrel having a larger diameter than said distal barrel.

2. The uterine tissue collector according to claim 1 wherein said at least one guide wire is disposed through at least one additional lumen formed through said cannula.

3. The uterine tissue collector according to claim 2 wherein said at least one additional lumen constrains movement of said at least one guide wire in a direction generally along a longitudinal axis of said cannula.

4. The uterine tissue collector according to claim 1 wherein a proximal portion of said at least one guide wire is pivotally attached about a fulcrum to a lever such that movement of said lever flexes the distal portion of said cannula.

5. The uterine tissue collector according to claim 1 and wherein said at least one guide wire comprises a pair of guide wires, wherein generally proximal movement of one of said guide wires causes flexing of said distal portion of said cannula in a direction different than that caused by generally proximal movement of the other guide wire.

6. The uterine tissue collector according to claim 5 wherein each said guide wire is disposed in a separate lumen formed in said cannula.

7. The uterine tissue collector according to claim 1 wherein said at least one guide wire is sufficiently stiff so as to be able to push as well as pull the distal portion of said cannula.

8. The uterine tissue collector according to claim 1 and comprising a suction device further comprising:
   a plunger element disposed inside said proximal barrel, said plunger element being adapted to sealingly slide inside said proximal barrel; and
   a plunger that passes through said plunger element, wherein when said plunger is pulled proximally and starts to enter said proximal barrel, said plunger is received at a shoulder formed in said plunger element, such that when said plunger is pulled further proximally, said plunger moves together with said plunger element and said plunger element serves as a new distal end of said plunger during sliding travel in said proximal barrel.

9. A uterine tissue collector comprising:
   a cannula which has an aperture formed therein through which tissue material can be sucked into a lumen formed in said cannula; and
   a suction device operative to suck tissue material into said lumen;
   characterized by said suction device comprising:
      a syringe comprising a distal barrel which extends from a proximal barrel, said proximal barrel having a larger diameter than said distal barrel;
      a plunger element disposed inside said proximal barrel, said plunger element being adapted to sealingly slide inside said proximal barrel; and a plunger that passes through said plunger element, wherein when said plunger is pulled proximally and starts to enter said proximal barrel, said plunger is received at a shoulder formed in said plunger element, such that when said plunger is pulled further proximally, said plunger moves together with said plunger element and said plunger element serves as a new distal end of said plunger during sliding travel in said proximal barrel.

* * * * *